(12) United States Patent
Sakurai

(10) Patent No.: US 7,802,477 B2
(45) Date of Patent: Sep. 28, 2010

(54) ORAL SENSATION MEASURING DEVICE FOR FOODS

(75) Inventor: Naoki Sakurai, Higashi-Hiroshima (JP)

(73) Assignee: Hiroshima University, Hiroshima (JP)

( * ) Notice: Subject to any disclaimer, the term of this patent is extended or adjusted under 35 U.S.C. 154(b) by 573 days.

(21) Appl. No.: 11/596,955

(22) PCT Filed: Feb. 18, 2005

(86) PCT No.: PCT/JP2005/002648

§ 371 (c)(1),
(2), (4) Date: Dec. 31, 2007

(87) PCT Pub. No.: WO2005/114136

PCT Pub. Date: Dec. 1, 2005

(65) Prior Publication Data

US 2008/0092674 A1 Apr. 24, 2008

(30) Foreign Application Priority Data

May 21, 2004 (JP) ............................. 2004-151798

(51) Int. Cl.
*G01N 29/04* (2006.01)
(52) U.S. Cl. ............................. 73/579; 73/597; 73/602; 73/866.5
(58) Field of Classification Search ................ 73/866.5, 73/602, 579, 597
See application file for complete search history.

(56) References Cited

U.S. PATENT DOCUMENTS

| 5,556,150 | A  | * | 9/1996  | Ampel ........................ 294/118 |
| 6,635,015 | B2 | * | 10/2003 | Sagel ......................... 600/300 |
| 6,720,185 | B2 | * | 4/2004  | Maeda et al. ................. 436/20 |
| 2002/0112547 | A1 | * | 8/2002 | Eltaib et al. ................... 73/808 |
| 2006/0034936 | A1 | * | 2/2006 | Lakkis et al. ............... 424/490 |

FOREIGN PATENT DOCUMENTS

JP 11190688 A 7/1999
JP 2001133374 A 5/2001

OTHER PUBLICATIONS

International Search Report, PCT/JP2005/002648, dated Jul. 12, 2005, ISA, Japanese Patent Office.

* cited by examiner

*Primary Examiner*—J M Saint Surin
(74) *Attorney, Agent, or Firm*—Sughrue Mion, PLLC

(57) ABSTRACT

A probe is inserted at a predetermined speed into a food to be measured, and vibrations created by the insertion are acquired by a piezoelectric element. The vibrations are displayed, and the pulse number per unit time on the basis of the insertion speed of the probe is calculated so that the oral sensation of the food is quantitatively specified with the pulse number.

20 Claims, 6 Drawing Sheets

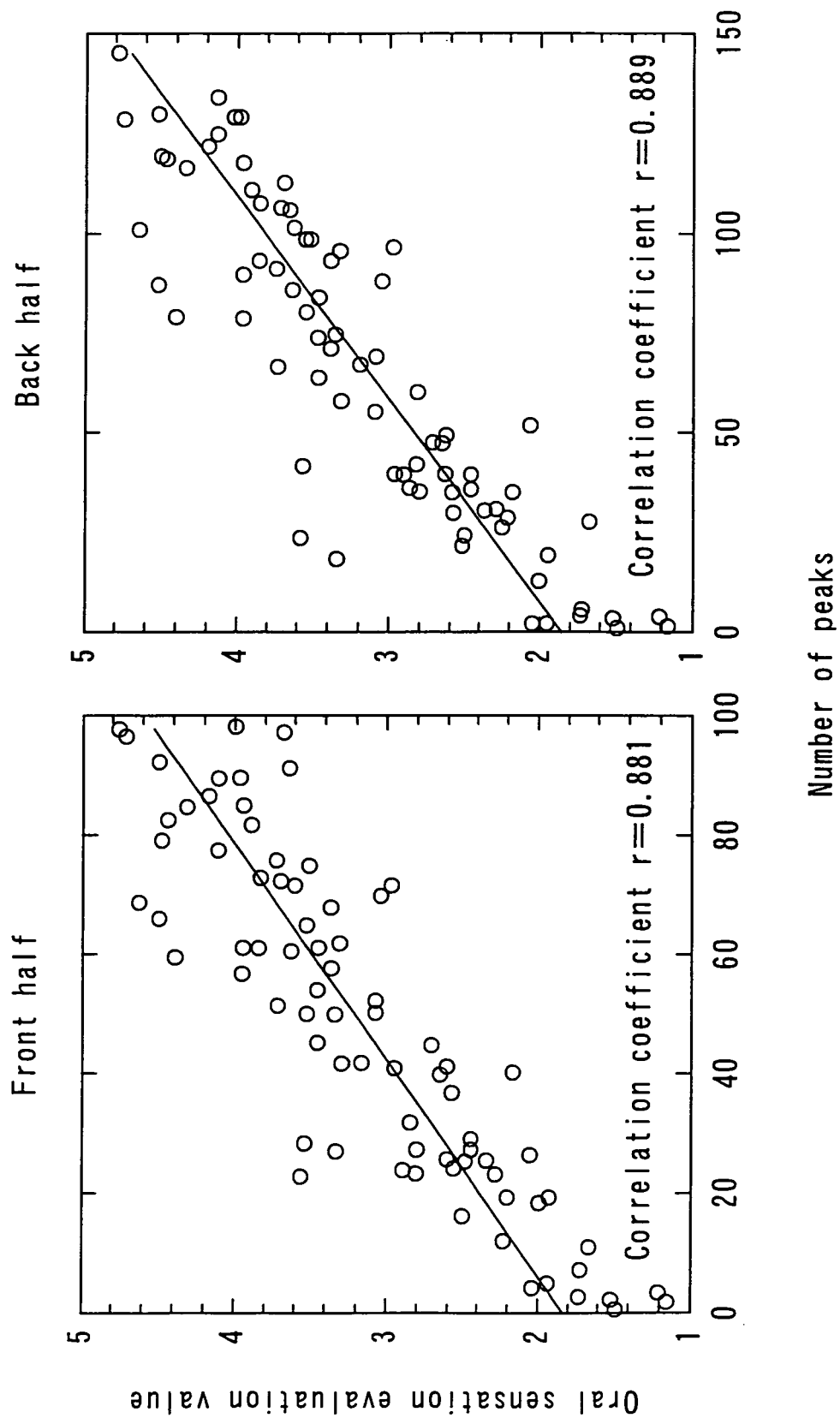

ORAL SENSATION MEASURING DEVICE FOR FOODS

This Application claims the benefit of 35 U.S. §371 for PCT Application No. PCT/JP2005/002648, which in turn claims foreign priority to Japanese Application No. 2004-151,798 filed May 21, 2004.

TECHNICAL FIELD

The present invention relates to an oral sensation measuring method for foods and an oral sensation measuring device for foods.

RELATED ART

We decide our preferences for foods or agricultural products on the basis of many factors such as taste, fragrance and color, in which oral sensation is a particularly important factor. Such oral sensation is derived from the mechanical properties (elasticity or viscosity) of foods. Thus, it is thought that the measurement of elasticity or viscosity of foods would quantify such oral sensation. In the case of noodles or pasta, oral sensation such as "stickiness" or "firmness" used customarily is measured quantitatively by pressing test materials such as noodles for a constant distance with pressing jig and then calculating the repulsive energy of the test material from the relationship between the distance and the pressing summation when the pressing jig is set back to the position where the stress of test materials on the pressing jig (repulsive force) becomes zero (see patent document No. 1, for instance).

However, oral sensation includes various kinds, including not only "stickiness" or "firmness". For instance, in the case of agricultural products, "crunchy" sensation when chewing fresh cucumbers or celery or "melting" sensation of ripe pears arouses our preferences greatly. This oral sensation cannot be expressed by the mechanical measurement such as conventional rheometer, and mainly evaluated by organoleptic assessment by human.

Also, in recent years, in order to measure Crispness that stands for "crunchiness" of porous foods such as cookies and snacks, the rupture energies at a predetermined frequency area are calculated by measuring rupture curves of these foods and analyzing their frequency area, and then the energies are quantified as the indicators of Crispness (See patent document No. 2, for instance).

Patent document No. 1: Japanese Patent Unexamined Publication No. Hei 11-190688 (Page 2-3, FIG. 1)

Patent document No. 2: Japanese Patent Unexamined Publication No. 2001-133374 (Page 2-4, FIG. 3)

For evaluating foods accurately with the help of organoleptic assessment, more than one skilled testers are required. Such skilled testers are trained for evaluating products such as wine and tobacco where sophisticated preferences are required, but such experts are not trained in the case of cheap agricultural products such as celery or cucumbers, so oral sensation is evaluated on the basis of a predetermined organoleptic assessment chart by non-skilled testers recruited in each case. So dispersion in evaluation is high and testers who conduct organoleptic assessment are not the same in many cases, and as a result it is difficult to compare the past result of measurement with the present result of measurement accurately.

In addition, in the way in which the rupture curve that is caused when the test material is destroyed as the way described in patent document No. 2, objects of measurement are limited to dry porous foods that contain less than several percents of water, and so there is a problem that the rupture curve doesn't show a significant correlation with its oral sensation when this way is applied to such foods that contain much water such as cucumbers or lettuce.

DISCLOSURE OF THE INVENTION

It is an object of the invention to quantify the oral sensation of foods such as "crunchy sensation" regardless of the water content.

For achieving the above object, the present invention relates to an oral sensation measuring method for foods, wherein said method comprises the process of:

inserting a probe at a predetermined insertion speed into a food to be measured and acquiring vibrations created at the time; and calculating the pulse number per unit time on the basis of said insertion speed of said probe from the signal strength of said vibrations so that said oral sensation of the food is quantitatively specified with said pulse number.

Also, the present invention relates to an oral sensation measuring device for foods, wherein:

said device comprises:

a probe for inserting at a predetermined insertion speed into a food to be measured and creating predetermined vibrations; and a vibration acquiring means for acquiring said vibrations; and said device is constituted for calculating the pulse number per unit time on the basis of said insertion speed of said probe from the signal strength of said vibrations so that said oral sensation of the food is quantitatively specified with said pulse number.

The inventors of the present invention have found that since in the signal strength of vibrations created when a probe is inserted into a food, several pulses are formed at a predetermined interval and these pulses also occur when touching said probe with fingers etc, said pulses are formed when said probe contacts with some kind of substances in said food. In other words, the inventors have found that said pulses are obtained after said probe contacts with cells or fibers in said food one after another and destroys them while said probe is inserted into said food.

On the other hands, the inventors have found that, although the occurrence frequency of said pulses differs depending on the kind of foods or the shape and size of the probe, if the probe used is specified and the occurrence frequency of the pulse, or the pulse number of each food is calculated, the oral sensation of each food can be quantified based on said pulse number because said oral sensation of foods is approximately proportional to the size or the density of the cells and fibers of said foods.

Thus, according to the present invention, the size and density of cells and fibers of said food correlated with the oral sensation of the food are measured from the pulse number of the signal strength of the vibrations obtained by inserting a probe into said food, and then the oral sensation of said food are quantified. Therefore, the oral sensation of said food such as "crunchy sensation" can be quantified regardless of the water content of said food.

BRIEF DESCRIPTION OF THE DRAWINGS

FIG. 6 is a graph illustrating the correlation between the value of the oral sensation by the method and device of the invention and the value of the oral sensation by estimators.

BEST MODE FOR CARRYING OUT THE INVENTION

From now, the details and other features and advantages of the present invention are described in detail on the basis of the best mode.

Figure 1:
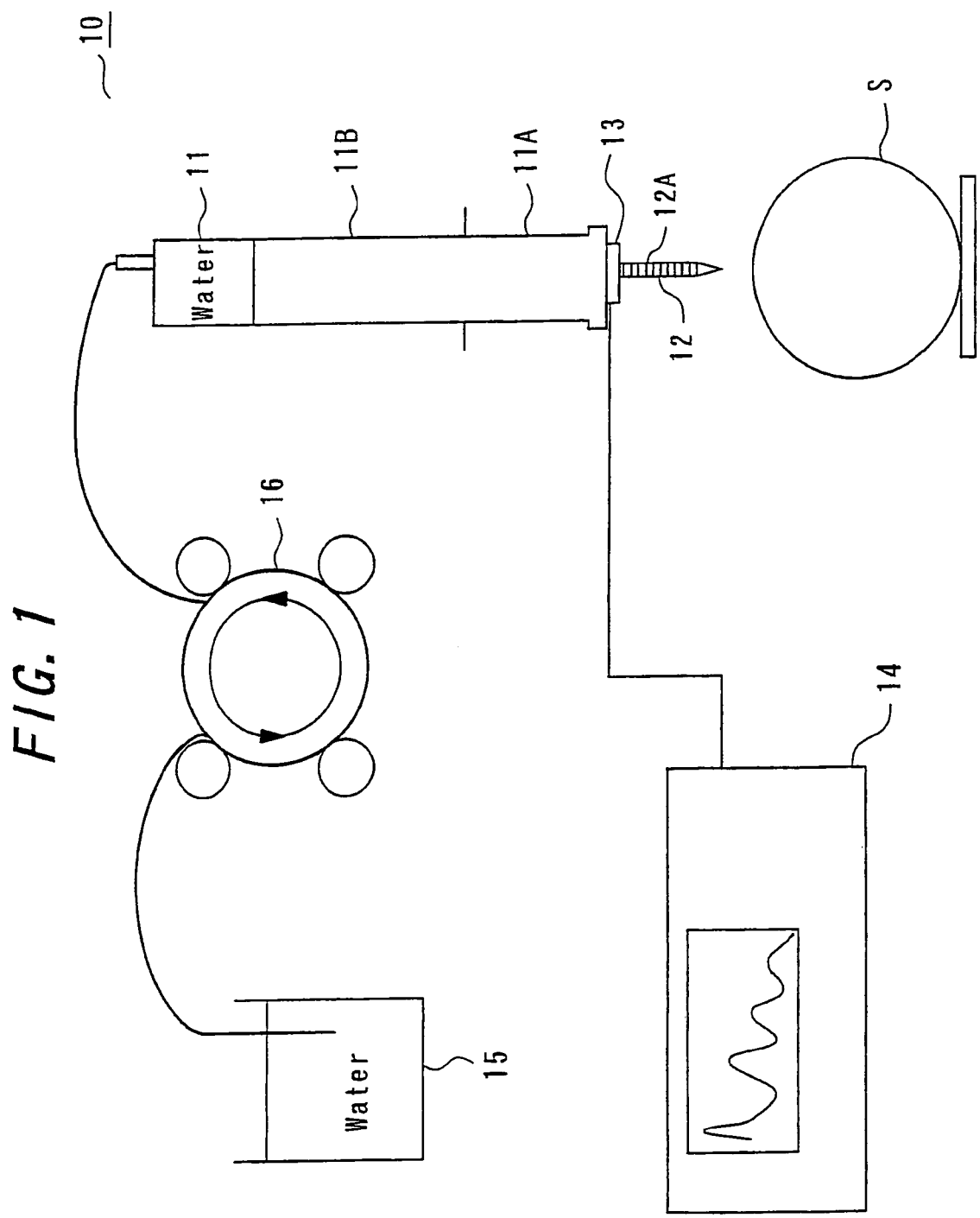
FIG. 1 is a block diagram illustrating an example of the oral sensation measuring device for foods of the invention.

FIG. 1 is a block diagram illustrating an example of the oral sensation measuring device for foods of the invention. An oral sensation measuring device for foods 10 shown in FIG. 1 is comprised of an injection syringe 11, a probe 12 which is provided at the tip of an inner tube 11A of this injection syringe 11 and has a groove portion 12A at the side, and a piezoelectric element 13 which is provided between the injection syringe 11 and the probe 12. In addition, since a water bath 15 is provided at the back of the injection syringe 11, this device is comprised wherein a probe 12 can be inserted into the food S by feeding water from the water bath 15 into the injection syringe 11 through a pump 16 and then lowering an inner tube 11A against an outer tube 11B by said pressure of water. Further, a computer 14 for analyzing the vibrations created by the insertion of the probe 12 into the food S, as more fully discussed hereinafter, is provided.

In addition, the shape of the probe 12 can be comprised of rectangular columns that have cross section of cylinder or polygon. Moreover, the probe 12 can also be comprised of members such as circular cone, triangular pyramid, and quadrangular pyramid. Further, the size thereof is set wherein sufficient large vibrations can be obtained depending on the kind of the food to be measured and the calculation of the pulse number can be carried out so that said oral sensation of the food can be measured accurately.

Again, a groove portion 12A provided at the side of the probe 12 is provided wherein sufficient large vibrations can be obtained depending on the kind of the food to be measured and the calculation of the pulse number can be carried out so that said oral sensation of the food can be measured accurately as mentioned above, and it is possible not only to provide said groove portion at the entire side as shown in the figure but also to provide at one part of said side, or it is also possible not to provide it at all.

However, when measuring the oral sensation of the food that contains much water, there is a case in which sufficient large vibrations cannot be obtained and so accurate oral sensation cannot be measured unless groove portions are provided at the side of the probe 12, so it is preferable to provide groove portions at least in some parts of the side of the probe 12 in these cases.

Next, the oral sensation measuring method for foods using the device 10 shown in FIG. 1 is described. At first, water is fed into the injection syringe 11 from the water bath 15 by the pump 16, and the inner tube 11A at the tip of which the probe 12 is attached is lowered and then inserted into the food S. The insertion speed at the time is not limited in particular, but is set at from 10 mm/min to 24,000 mm/min preferably. In this case, whether the water content of the food S is much or not, sufficiently large vibrations can be obtained and fully accurate oral sensation can be measured by measuring accurate pulse number. By the way, the upper limit of said 24000 mm/min is approximately equivalent for the upper limit of chewing speed of human.

When the probe 12 is inserted into the food S, the probe 12 becomes vibrating because the probe 12 contacts with the cells or fibers in the food S or destroys them. In the present invention, these vibrations are sent to the computer 14 after acquired by a piezoelectric element 13 and converted to electric signal.

Figure 2:
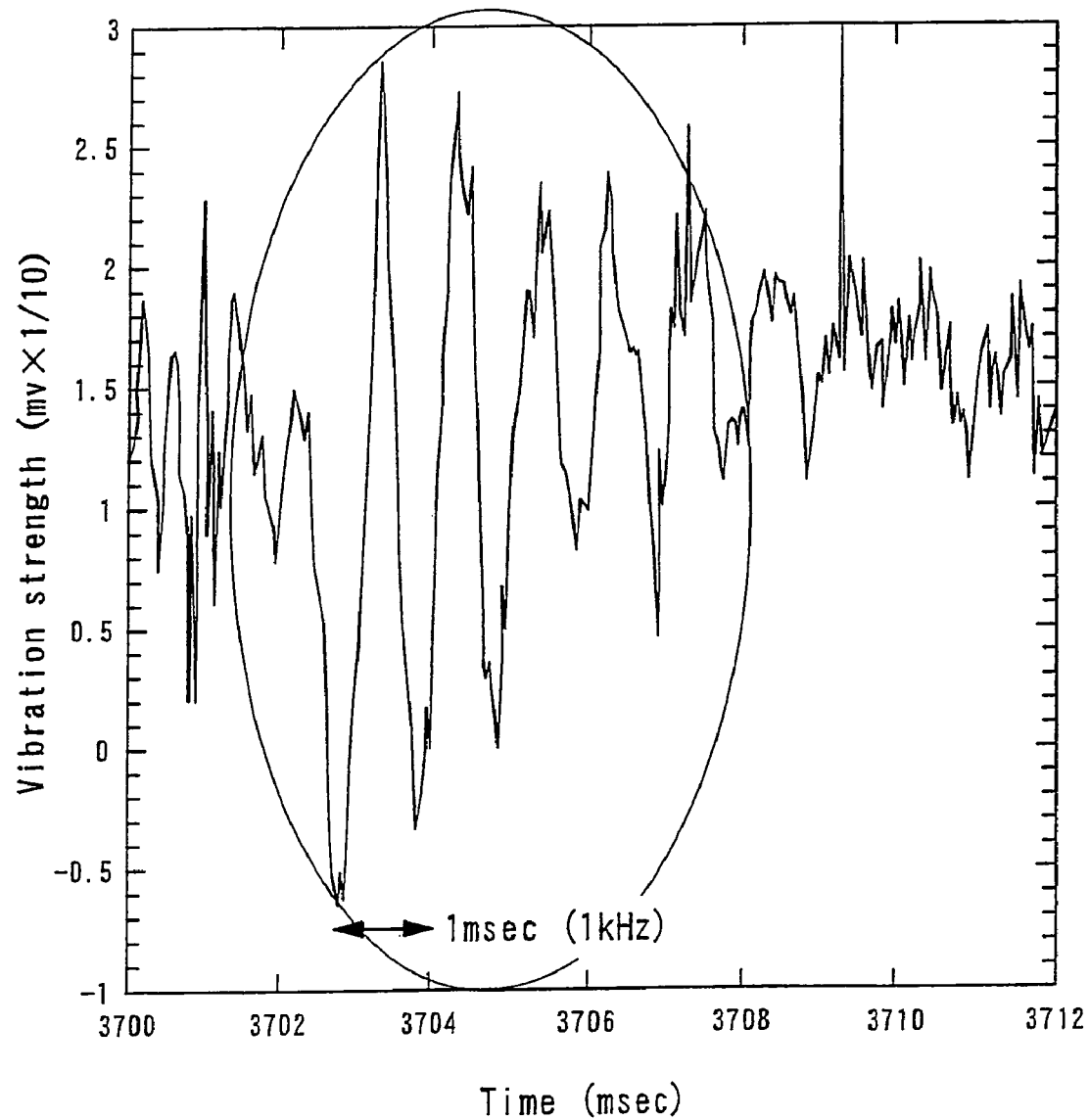
FIG. 2 is a graph illustrating an example of the signal strength of the vibrations obtained in the oral sensation measuring method for foods of the invention.

On the computer 14, said vibrations is displayed as shown in FIG. 2 based on said electric signal about said vibrations. Now, FIG. 2 extracts and shows part of signal strength of said vibrations. In the signal strength of the vibrations shown in FIG. 2, encircled damped vibrations are equivalent for the aforesaid vibrations that are derived from one contact with said cells and said fibers or destruction of them when probe 12 is inserted into the food S.

On the other hand, considering the fact that the oral sensation of the food S is approximately proportional to the size of cells and fibers of the food S or the density thereof, by setting said damped vibrations as one pulse and then calculating the pulse number per unit time in said signal strength of said vibrations, the oral sensation of the food S can be quantified using said pulse number.

However, there is a case in which different pulse numbers are obtained depending on the kind of foods even if the oral sensation is similar, so it is preferable to examine the correlation between the oral sensation and the pulse number in each food and then quantify the oral sensation from the pulse number in each food based on this correlation.

Figure 3:
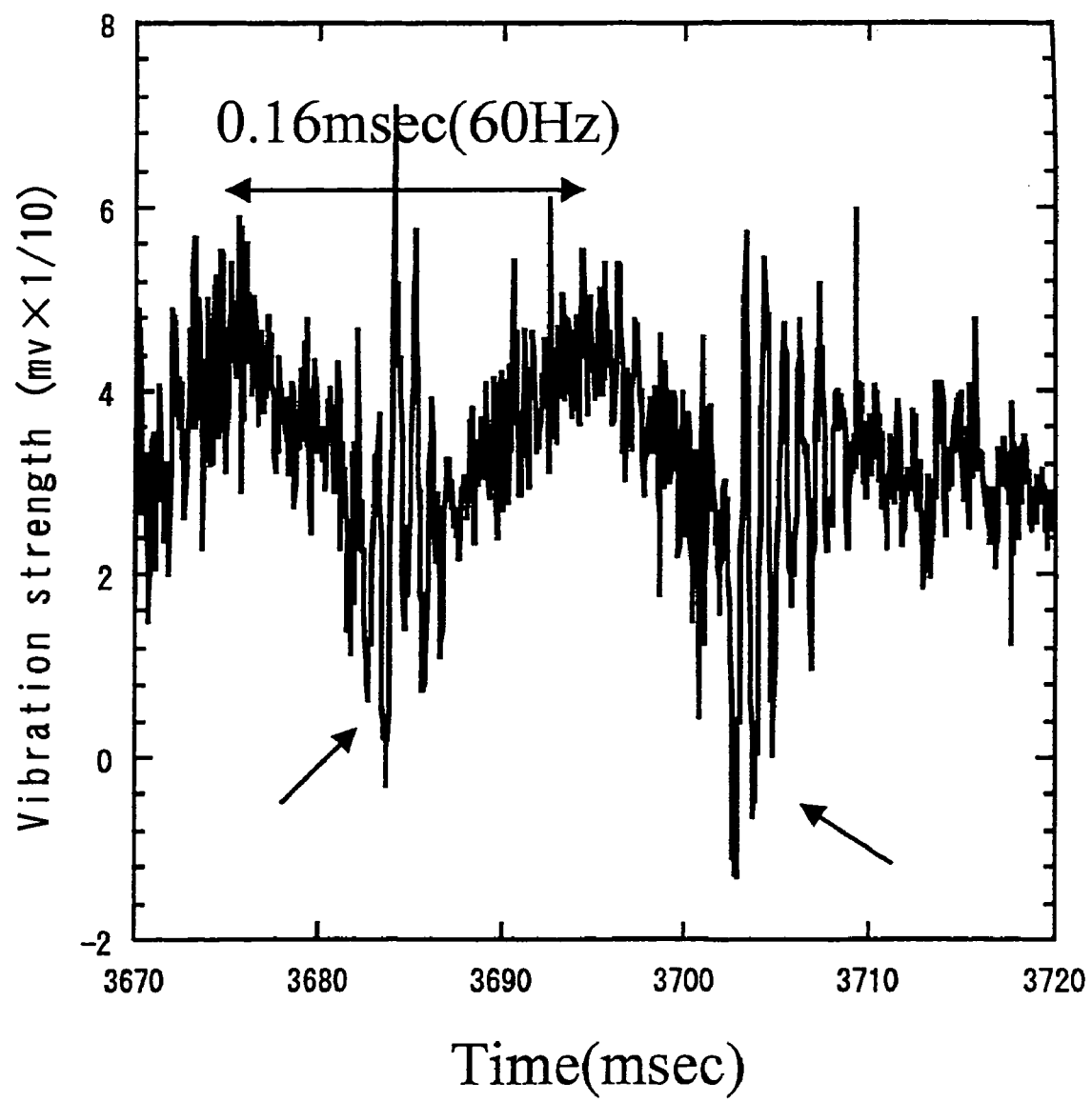
FIG. 3 is a graph illustrating an example of the signal strength of the vibrations including power-supply noise, obtained in the oral sensation measuring method for foods of the invention.
Figure 4:
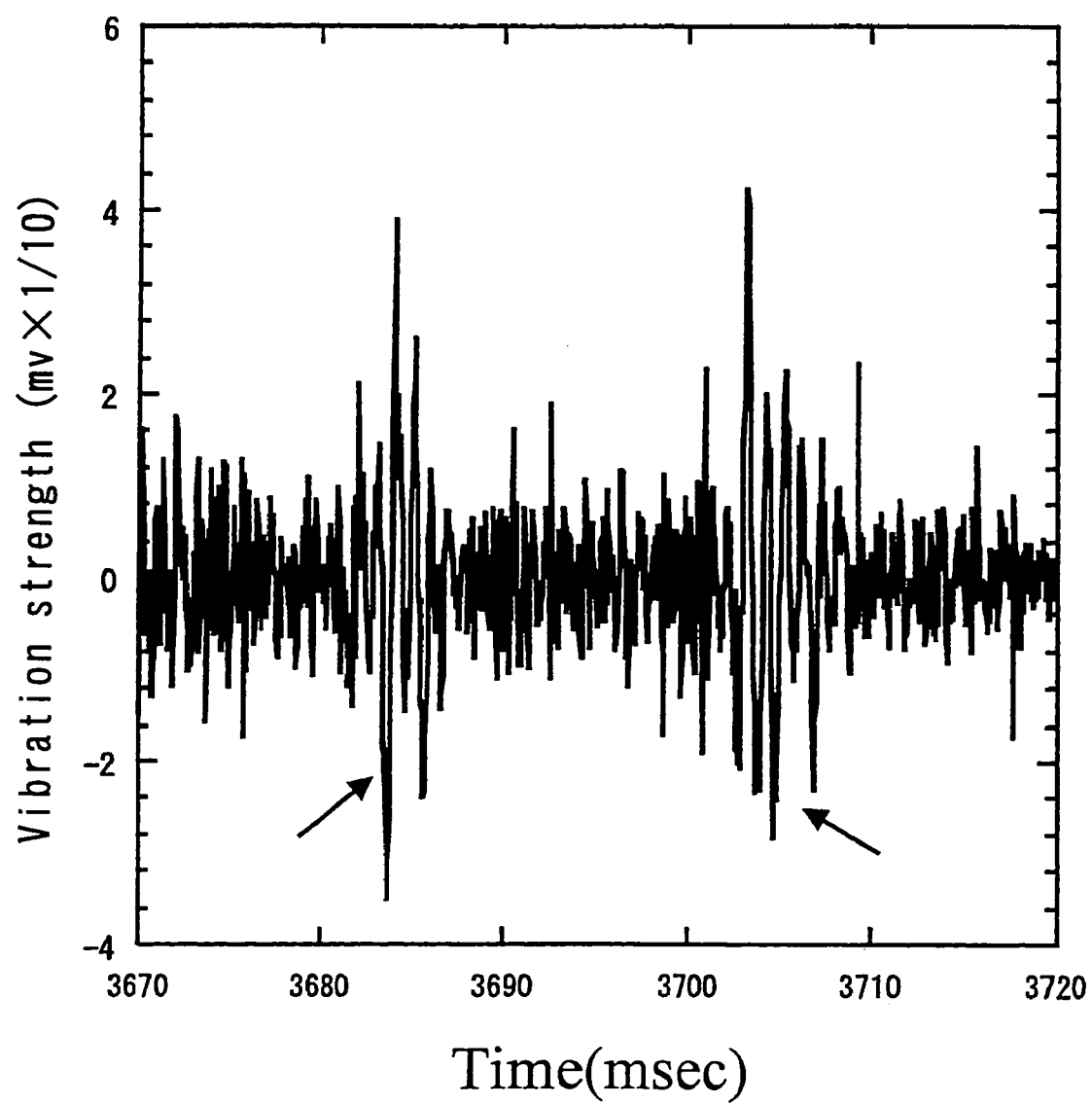
FIG. 4 is a graph illustrating an example of the signal strength wherein the power-supply noise is removed from the signal strength shown in FIG. 3 by filtering process.

In addition, since there is a case in which information other than the information about the oral sensation of the food S overlaps in said electric signal from a piezoelectric element 13 in the actual measurement of the oral sensation, it is preferable to display only the information about said oral sensation as mentioned above after carrying out filtering process when loading said electric signal onto the computer 14. By this filtering process, it is possible to get only the information about the oral sensation shown in FIG. 4 wherein said power-supply noise is removed from the signal strength overlapped with the power-supply noise shown in FIG. 3.

Also, since frequency band of the information about said oral sensation of the food S varies depending on the sort of the food S and shape and size of the probe 12, only the information about said oral sensation will be filtered in said filtering process.

Said unit time that acts as a basis for measuring the pulse number are not limited in particular, but preferably it would be set larger than 100 μm/insertion speed of the probe 12. For example, since the average size of the cells of foods such as fruits containing much water is about 100 μm, when said unit time is shorter than the time obtained by dividing said size by the insertion speed of the probe 12 and thereby the probe 12 cannot contact with the cells etc in the foods or cannot destroy them, said damped vibrations in the signal strength of the vibrations shown in FIG. 2 that specify the oral sensation cannot be calculated as a result.

However, as mentioned above, since the preferable insertion speed of the probe 12 is from 10 mm/min to 24000 mm/min and so 100 μm/insertion speed of the probe 12 equals from $2.5*10^{-4}$ to 0.6 seconds in this case, the oral sensation of foods can thoroughly quantitated with said pulse number if the unit time is set one second in particular and then said pulse number during one second is calculated in the present invention.

By the way, in a preferred embodiment of the present invention, it is possible not only to measure the pulse number as damped vibrations directly from the signal strength of the vibrations shown in FIG. 2, but also to measure the pulse number after analyzing in the way hereinafter described.

Figure 5:
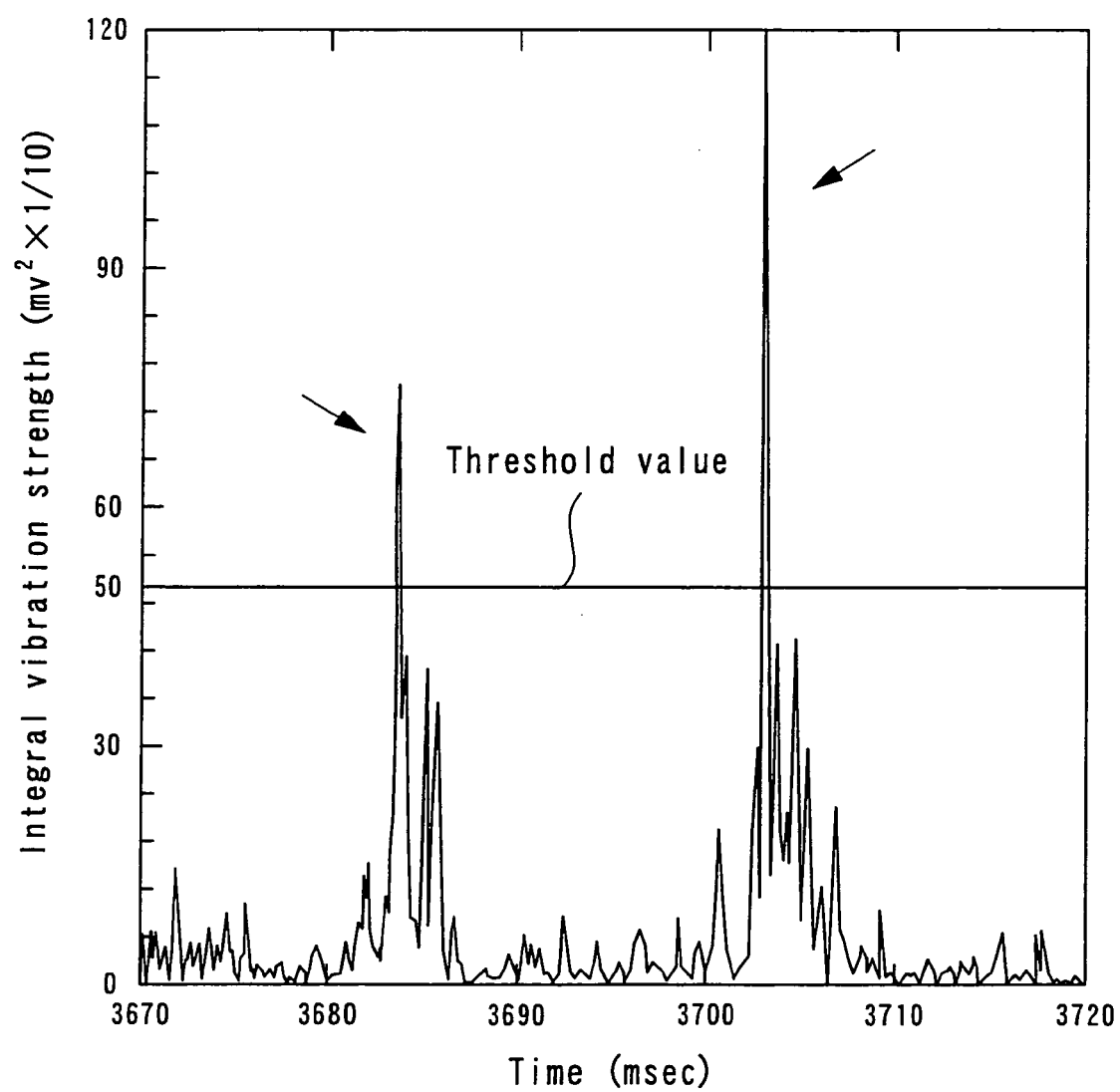
FIG. 5 is a graph illustrating an example of integral signal obtained in the oral sensation measuring method for foods of the invention.

At first, by squaring the signal strength as shown in FIG. 2 by its amplitude strength and integrating the obtained signal strength by the duration of said damped vibrations, graph of the time and integral signal as shown in FIG. 5 are made. Since not only the peak derived from said damped vibrations but also the peak derived from the vibrations other than said damped vibrations appears in FIG. 5, only the peak derived from said damped vibrations should be selected by setting a predetermined threshold level as shown in FIG. 5, and then said pulse number about said damped vibrations can be measured by measuring this peak number. Therefore, the oral sensation of the food S can be quantified by measuring said peak number.

Here, the amplitude of said peak derived from said damped vibrations is equivalent to the energy required when the probe 12 contacted or destroyed the cells or fibers in foods. Therefore, by getting several peaks derived from said damped vibrations and averaging them, the hardness of said foods can be quantified. In addition, since different peak energies are obtained depending on the kind of foods even if the hardness is similar, it is preferable to examine the correlation between oral sensation and peak energy in each food and then to quantify the hardness of the food from the peak energy in each food based on this correlation.

EXAMPLES

By using the above oral sensation measuring device for foods and the oral sensation measuring method for foods of the invention, test on the oral sensation of Japanese persimmon was carried out. The insertion time of the probe was set for 5 seconds and test on the oral sensation was carried out in two times consist of the first half 2.5 seconds and the second half 2.5 seconds. Besides, the measurement of the pulse number derived from the damped vibrations by the insertion of the probe was substituted by measuring the peak number of the integral signal according to the above preferable aspect. Further, in order to justify the quantitation of oral sensation of said Japanese persimmon in said test on the oral sensation, crunchy sensation to be specific, correlation with the oral sensation, or crunchy sensation by the actual testers was examined.

The evaluation of the oral sensation by testers was carried out in the way that 3 male and 3 female eat the portion of Japanese persimmon used in the test where a probe is inserted and keep the score from level 1 to level 5 depending on the hardness. Here, the increase in level means the increase in said hardness of Japanese persimmon, or the increase of crunchy sensation.

FIG. 6 is a graph showing the correlation between the test on the oral sensation of Japanese persimmon according to the invention and the test on the oral sensation by estimators. It is found that the test on the oral sensation according to the invention has a high correlation with the test on the oral sensation by estimators in both the first half and the second half of the insertion of the probe. In other words, the oral sensation concerning the crunchy sensation of Japanese persimmon can be quantified by calculating the pulse number derived from the damped vibrations that is obtained by the insertion of said probe into Japanese persimmon according to the present invention.

By the way, although not specified particularly in the example, it has turned out that the oral sensation of foods that contain extremely much water such as melon can also be quantified by calculating the pulse number derived from the vibrations that is created by the insertion of the probe.

Although the invention is described in detail through some examples based on the mode of the invention hereinbefore, it is not intended to be limited to the above description because every modifications and changes may be made therein without departing from the category of the present invention.

The invention claimed is:

1. An oral sensation measuring method for foods, comprising: inserting a probe at a predetermined insertion speed into a food to be measured and acquiring vibrations created at the time; and calculating the pulse number per unit time on the basis of said insertion speed of said probe from the signal strength of said vibrations so that specifying said oral sensation of the food quantitatively with said pulse number;
wherein said insertion speed of said probe is from 10 mm/min to 24000 mm/min.

2. The oral sensation measuring method for foods according to claim 1, wherein said unit time is set faster than 100 μm/said insertion speed.

3. The oral sensation measuring method for foods according to claim 2, characterized in that said unit time is one second.

4. The oral sensation measuring method for foods according to claim 1, wherein in that said calculating of said pulse number comprises the processes of: obtaining a graph of the time and integral signal by squaring said signal strength and integrating the obtained signal strength by the duration of said vibrations; and setting a predetermined threshold level for said integral signal and calculating the peak number of said integral signal that exceed said threshold and then setting this pulse number as said pulse number.

5. The oral sensation measuring method for foods according to claim 4, wherein said method further comprises the process of quantitating the hardness of said food from a value of energy of said peaks in said integral signal that exceed said threshold.

6. The oral sensation measuring method for foods according to claim 1, wherein said signal strength of said vibrations is obtained by filtering the obtained vibrations by the insertion of said probe by a predetermined frequency band.

7. The oral sensation measuring method for foods according to claim 1, wherein said signal strength of said vibrations is acquired by a mechanical electric signal transformation element that is provided next to said probe.

8. The oral sensation measuring method for foods according to claim 1 wherein said probe is a rectangular column which has cross section of cylinder or polygon and has a groove portion at one part or all parts of its side.

9. The oral sensation measuring method for foods according to claims 1 wherein said probe is a rectangular column which has cross section of cylinder or polygon and has no groove portion at its side.

10. The oral sensation measuring method for foods according to claim 1, wherein said oral sensation of foods is crunchy sensation of foods.

11. An oral sensation measuring device for foods comprising: a probe for inserting at a predetermined insertion speed into a food to be measured and creating predetermined vibrations; and a vibration acquiring means for acquiring said vibrations; wherein for calculating the pulse number per unit time on the basis of said insertion speed of said probe from the signal strength of said vibrations so that said oral sensation of the food is quantitatively specified with said pulse number;

wherein said insertion speed of said probe is from 10 mm/min to 24000 mm/min.

12. An oral sensation measuring device for foods according to claim 11, characterized in that said unit time is set faster than 100 μm/said insertion speed.

13. The oral sensation measuring device for foods according to claim 12, characterized in that said unit time is set one second.

14. The oral sensation measuring device for foods according to claim 11, characterized in that said calculating of the pulse number comprising the processes of: obtaining a graph of the time and integral signal by squaring said signal strength and integrating the obtained signal strength by the duration of said vibrations; and setting a predetermined threshold level for said integral signal and calculating the peak number of said integral signal that exceed said threshold and then setting these pulse number as said pulse number.

15. The oral sensation measuring device for foods according to claim 14, characterized in that said device quantitates the hardness of said foods from a value of energy of said peaks in said integral signal that exceed said threshold.

16. The oral sensation measuring device for foods according to claim 11, characterized in that said signal strength of said vibrations is obtained by filtering the obtained vibrations by the insertion of said probe by a predetermined frequency band.

17. The oral sensation measuring device for foods according to claim 11, characterized in that said vibration acquiring means is a mechanical electric signal transformation element that is provided next to said probe.

18. The oral sensation measuring device for foods according to claim 11, characterized in that said probe is a rectangular column which has cross section of cylinder or polygon and has a groove portion at one part or all parts of its side.

19. The oral sensation measuring device for foods according to claim 11, characterized in that said probe is a rectangular column which has cross section of cylinder or polygon and has no groove portion at its side.

20. The oral sensation measuring device for foods according to claim 11, characterized in that said oral sensation of foods is crunchy sensation of foods.

* * * * *